United States Patent [19]

Coombes

[11] 4,299,812
[45] Nov. 10, 1981

[54] IMMUNOASSAY OF THYROXINE IN NEONATES USING DRIED BLOOD SAMPLES

[75] Inventor: Robert F. Coombes, Walnut, Calif.

[73] Assignee: Diagnostic Products Corp., Los Angeles, Calif.

[21] Appl. No.: 964,593

[22] Filed: Nov. 29, 1978

[51] Int. Cl.³ .................. G01N 33/48; G01T 1/00
[52] U.S. Cl. ................................ 424/1; 23/230 B; 424/12; 435/4; 435/7
[58] Field of Search .............. 424/1, 12; 23/230 B; 435/4, 7

[56] References Cited

U.S. PATENT DOCUMENTS

| | | | |
|---|---|---|---|
| 3,716,632 | 2/1973 | Fader et al. | 424/1 |
| 3,745,211 | 7/1973 | Brown et al. | 424/1 |
| 3,928,553 | 12/1975 | Hollander | 424/1 |

Primary Examiner—Benjamin R. Padgett
Assistant Examiner—Christine M. Nucker
Attorney, Agent, or Firm—Joseph E. Mueth

[57] ABSTRACT

In the immunoassay of thyroxine using dried blood samples spotted on filter paper, the assay in this invention is run at a pH of 9.2 to 10.0, preferably at about 9.5, rather than the pH range of about 8.4 to 8.7 generally used in the art. The advantage of this higher pH range is that more accurate results are obtained with neonatal specimens. An additional advantage is that the blank or nonspecific binding is lower for many immunoassay procedures.

36 Claims, No Drawings

IMMUNOASSAY OF THYROXINE IN NEONATES USING DRIED BLOOD SAMPLES

BACKGROUND OF THE INVENTION

The neonatal period is critical for brain development. Neonatal hypothyroidism, if undetected in the first months of life, will usually lead to mental retardation. If the condition is detected and treatment begun early enough, the child will develop normal intelligence in most cases. For this reason screening of all newborns for hypothyroidism is rapidly becoming a routine practice in many places. A common assay for the detection of hypothyroidism in neonates is radioimmunoassay of thyroxine (T4) concentration using samples of dried blood collected on filter paper.

Radioimmunoassay (RIA) is an analytical method which uses an antiserum that reacts specifically with the hormone to be quantitated, a radioactively labeled form of that hormone which also reacts with the antiserum and thus competes with sample hormone for available antibody binding sites, a separation method which allows one to isolate and count either the antibody bound labeled hormone or the free labeled hormone after a competitive reaction, and calibrators which contain various known amounts of the hormone being quantitated. The procedure involves mixing antibody, radioactive hormone, and either unknown or calibrator in each of a number of tubes which are run in the same assay. The hormone in either calibrator or unknown sample in each assay tube then competes with labeled hormone for the available antibody binding sites during an incubation period. The percentage of labeled hormone binding to the antibody diminishes as the concentration of unlabeled hormone in the samples increases. After separation of bound and free hormone, the labeled hormone is counted in order to determine the amount of radioactivity present. By comparing data obtained from tubes which contained calibrators to data obtained from tubes which contained unknowns, the concentration of hormone in the unknowns is determined.

Radioactivity is not the only way of labeling the hormone. Other possibilities include a flourescent label, a luminescent label, and an enzyme label. The more general term which includes all of these labels is "immunoassay."

The sample collection method utilizing blood samples from a heel prick spotted on filter paper and dried is convenience for screening of neonates. It is most widely used for this purpose rather than the assay of serum or plasma which is used for adults and older children. Serum assays are older and have met the test of wide experience. Serum assay is therefore the method of choice for comparison of results in order to validate the relatively new blood spot assays. It is common to compare results obtained using blood spot samples to results obtained using serum samples. However, investigators ordinarily run such validation experiements with adult blood spots and adult serum samples rather than using neonates. This is due to the difficulty in obtaining specimnents from neonates for experimental purposes.

Even though blood spot assays generally correlate well with serum assays when adult subjects are used a review of the literature revealed that mean values for neonatal subjects with serum assays are much higher than mean values for blood spot assays. To demonstrate this inconsistency, the following Table was prepared to show the mean value of nine literature studies using serum samples and four studies using blood spot assays.

TABLE I

| Mean T4 Serum Conc., ug/dl | Age in Days | Type of Sample | Reference |
|---|---|---|---|
| 15.0 | 3–5 | Serum | 1 |
| 15.5 | 1–3 | Serum | 2 |
| 16.2 | 1–2 | Serum | 3 |
| 16.4 | 3–4 | Serum | 4 |
| 16.6 | 3–4 | Serum | 5 |
| 17.2 | 3 | Serum | 6 |
| 20.2 | 2 | Serum | 7 |
| 20.7 | 3 | Serum | 8 |
| 21.9 | 2 | Serum | 9 |
| 11.0 | 3–6 | Blood Spot | 10, 4 |
| 12.4 | Not Specified | Blood Spot | 11 |
| 12.6 | 3 | Blood Spot | 12, 4 |
| 12.81 | Not Specified | Blood Spot | 13 |

If the mean values from the nine studies using serum RIA in the above table are averaged, we obtain a value of 17.7 ug/dl for neonates in serum assays. The average neonatal T4 serum concentration calculated from the four studies which assayed dried blood spots is only 12.2 ug/dl. The difference in the blood spot assays and the serum assays is dramatic. Serum assays give on the average of 45.1% higher values than blood spot assays, and there is no overlap between blood spot means and serum assay means for the studies in the Table. This indicates that there is some inherent error in one of the two types of methodologies, more significant than expected variations due to differences in potencies of the calibrators or demographic characteristics of the different populations used for each study.

I have now discovered that in the RIA of T4 in neonates using dried blood collected on filter paper as samples, a dramatic increase in assay values for neonatal samples (but not necessarily for adult samples) occurs when the pH is raised to the region of about 9.2 or above, with an upper limit of possible pH being determined by capability of antiserum binding at high pH or stability of reagents. When the assay of this invention is run at a pH of 8.6, which is approximately the pH of all other procedures of which I am aware, the mean value obtained for neonatal samples is about the same as are obtained with other blood spot assays. As discussed above, serum assays give values about 45% higher than this. When the assay of this invention is run at a pH of 9.2 through 10.0, the mean value of T4 concentration for neonatal samples is approximately constant and is within the range of mean values reported for serum assays.

The RIA of this invention includes a determination of the "blank" or "nonspecific binding" in which the antiserum is omitted from two assway tubes in order to determine to what extent radioactivity is absorbed to the precipitate which contains the antibody-bound radioactivity in the calibrator and unknown tubes. At pH 8.6 the blank is over 10% of the total counts added to the tubes, whereas the blank in the higher pH region drops to about 5% (which probably represents mechanical hold-back rather than nonspecific absorption). This reduction in blank is a desirable effect which accompanies the increase in assay values for neonates at pH of at least 9.2.

The present invention provides a substantial improvement in the art, and its widespread adoption is to be anticipated.

SUMMARY OF THE INVENTION

Briefly, the present invention comprises incubating assay tubes each of which contain a labeled form of the thyronine, calibrator unknown sample, and an antiserum to the thyronine, with or without other reagents, at a pH above 8.9 and high enough to cause the assay to yield, with some patient's samples, different and more accurate results than are obtained in the same assay at pH 8.9, and below pH which causes excessive interference with the antigen-antibody reaction or with the separation of bound from free antigen, or substantial decomposition or instability of the reagents.

It is an object of this invention to provide any improved immunoassay. More particularly, it is an object of my invention to provide an improved ammunoassay of thyroxine in neonatals using dried blood samples.

In particular, it is an object of this invention to provide more accurate results with said neonatal specimen.

The other object and advantages of this invention will be apparent from the more detailed descriptions which follows.

DESCRIPTION OF PREFERRED EMBODIMENT

While not bound by an theory, it is believed that the increase in assay values for neonates is the result of greater solubility of T4 at the higher pH region which reduces the tendency to associate nonspecifically with various things, including something that causes the neonatal samples to read low at lower pH. Higher pH removes the interference by increasing the solubility and the hydrophilicity and reducing the tendency to associate with things nonspecifically (and the lipophilicity) of T4. This is analogous to the concept of hydrophilic versus lipophilic character well known in the field of design of new drugs, which need to exhibit lipophilicity in order to cross cell membranes by passive absorption through the lipid barrier. The T4 molecule has a large aromatic moiety which causes its hydrophobic tendencies. At higher pH, increased net ionic charge enhances its hydrophilicity which counteracts the tendency for hydrophobic associations.

The probable explanation for increased hydrophilicity of T4 at high pH is well known. The ionizable groups on the T4 molecule are a carboxyl group with a pK of about 2.2, an aromatic hydroxyl group with a pK of about 6.6, and an alpha-amino group with a literature pK of about 10.1. Thus at pH 8.6 there is a net negative charge of $-1$ on most T4 molecules at any one instant. When the pH is increased towards the pK of the amino group, a greater percentage of T4 molecules carry a neutral amino group and therefore a net charge of $-2$; since "like dissolves like," the greater polarity of the molecules with greater net negative charge causes them to be more soluble in the polar solvent, water. At pH 9.2, assuming the literature pK of 10.1 to be correct, about 12.5% of the molecules carry a net charge of $-2$ and 87.5% carry a net charge of $-1$ at any given instant. Since the ionic states exist in rapid equilibrium, all of the molecules carry a net charge of $-2$ 12.5% of the time at pH 9.2. Apparently this is enough to cause a dramatic decrease in nonspecific interference in the assay.

This, the foregoing theory explains the discrepancy between serum assay mean values and blood spot assay mean values for neonatal samples. There is a source of interference in the neonatal samples which is related to the hydrophobic character of T4. This interference can be removed by using a pH that is high enough to sufficiently reduce the tendency towards hydrophobic associations. The critical pH, at least for our particular methodology, has been determined to be about 9.2 with an error of measurement of 0.1. For a different methodology the critical pH may be slightly different, but will be somewhere in the general vicinity of the pK of the alpha-amino group.

This invention may also apply to some methodologies of T4 determination on serum samples or adult blood spot samples, particularly if a protocol requires a larger samples size than most RIA procedures. An example of a methodology which usually will require a larger sample size, and concomittant increased risk of nonspecific interference, is enzyme immunossay as well as other nonisotopic immunossay. In addition, even classical RIA procedures for serum samples as currently known in the art would probably benefit from use of this invention, because an occasional sample is likely to contain an interference which would be removed if the assay were run at a higher pH. Additionally, since T3 is structurally very similar to T4, the invention applies here. It should be noted that T3 RIA has a larger sample size requirement than a T4 determination, and T3 values have a larger methodology-to-methodology variation than is known in T4 RIA.

The antiserum in T4 RIA can be produced in a variety of animals by immunizing with a conjugate of thyroxine or thyroxine analog to a large molecule such as a protein. The preparation of the conjugate, immunization procedure, and selection of animals is all done by a variety of methods generally known in the art.

The tracer is most commonly a radioactive form of T4 in which one of the iodine atoms is replaced by iodine-125. Other substitutions of radioactive isotopes such as iodine-131 or tritium may be used, or a radioactive derivative of T4 could be used, attaching an unnatural moiety to the T4 molecule in such a way that performance of the tracer is not greatly impaired in the assay. Such a derivitized tracer need not be of the radioactive type. The label may be a fluorescent or luminescent moiety, or it could be an enzyme. In the case of an enzyme label, an appropriate enzyme substrate must be included in the assay.

The calibrators are prepared by the general method known in the art wherein calibrator specimens are prepared having various concentrations of T4. The calibrators may either be prepared in whole blood and spotted on filter paper, or they may be in liquid form in buffer or serum.

The procedure involves some method of freeing T4 from proteins such as albumin and TBG which bind to the hormone. This may be a pre-treatment with acid or base or an alcohol. It also may be effected by an additive to the buffer which competitively inhibits T4 binding to interfering proteins. Competitive inhibitors widely used in the art include sodium salicylate and ANS. Also a combination of pre-treatment and competitive inhibition may be used.

The sample, or processed sample, the antiserum, the radioactive tracer, and possibly other reagents such as buffer or precipitating antibody or competitive inhibitors are then incubated together at temperatures known in the art (generally 4° C. to 50° C.). The reaction is buffered in this invention at a pH known to give accurate results (i.e., pH 9.2 or above, but not so high as to interfere excessively with antibody binding to T4, or to cause stability problems; preferably at a pH not too close to the critical pH so as to avoid problems caused by small errors in pH; a pH of about 9.5 is suitable).

The separation of bound and free hormone after the incubation may be accomplished by a variety of means, including second antibody (also called precipatating antibody) an adsorbant such as charcoal or talc, precipatating solution such as polyethylene glycol or ammonium sulfate, ion exchange, or use of solid phase antibody attached to plastic, glass, or polymer; or polymerized antibody, or solid phase second antibody.

The amount of bound (or free) labeled T4 in each sample reaction may be determined, in the case of RIA, by counting radioactivity in the precipitate or solid phase (or the supernate). By comparing the data obtained from the calibrator reactions to the data obtained from the unknown sample reactions, the amount of T4 in the unknown samples can be determined. This is ordinarily done by first plotting the data obtained from the calibrator reactions in order to obtain a calibration curve. In the case of nonisotopic labels, similar calculations are made based on data obtained from such instruments as a spectrophotometer or a fluorometer.

In accordance with this invention, there can be provided a kit for the assay of T4 which includes labeled T4, antiserum to T4, and calibrators containing specified amounts of T4. The kit may further include a buffer which maintains a pH of 9.2 or higher, preferably about 9.5, in the incubation mixture, or such a buffer may be included in the other reagents. Also a competitive inhibitor or basic, acidic, organic pre-treatment solution may be included. The kit may also include other materials useful in the assay, such as a precipitating antiserum and/or PEG for separating antibody-bound from free T4.

The invention will be described with respect to the following examples, but the scope of the invention is not to be limited thereby.

The following is an illustrative protocol for the immunoassay of T4 in neonates using blood samples spotted and dried on filter paper. The example uses a radioactive label, but this does not imply such limitation to the invention. It is also not to be implied that the invention is limited to neonatal blood spot assays, because as discussed above it will apply to other serum assays for similar reasons, that it is applicable in the exemplary assay. It also is not intended to be limited to T4 assays, because for example it will apply to T3 immunoassays for reasons discussed above. In fact it will be applicable to any assay of an antigen possessing an ionizable group and having low solubility or high hydrophobic character particularly above or below the pH corresponding to the pK of the ionizable group.

EXAMPLE

Preparation of 0.1 N NaOH and 1 M Tris Buffer

A solution of 0.1 N NaOH and another solution of 1 M tris, 0.1 M boric acid are made. The pH of the tris buffer is adjusted so that when two parts of the 0.1 N NaOH and one part of the tris are mixed, the resulting pH is 9.5. These reagents are then stored until used in the Neonatal T4 RIA.

Procedure for Neonatal T4 RIA using dried blood spot samples (at pH 9.5).

A. Standard curve
1. Label sixteen tubes, two with each of the following labels:
   T, B, MB, 1, 4, 10, 16, 32.
2. Punch and add one ⅛" (3.2 mm) circle of the O ug/dl blood spot to each of the tubes prepared in step 1 except the T tubes.
3. Add 200 ul 0.1 N NaOH to each tube except the T tubes.
4. Add 25 ul of O ug/dl calibrator to the B and MB tubes,
   25 ul of 1 ug/dl calibrator to the tubes labeled "1,"
   25 ul of 4 ug/dl calibrator to the tubes labeled "4,"
   and so on up to the 24 ug/dl calibrator.
5. Vortex all tubes. Shake the rack 30 or more times every 15 minutes for one hour, or place on a mechanical shaker.
6. Add 100 ul of the tris buffer per tube. Shake the rack vigorously 30 or more times.
7. Add 50 ul of 125-I T4—goat anti-rabbit gamma globulin mixture to all tubes. Remove the T tubes for counting total counts.
8. Add 50 ul antiserum to all tubes except the B (blank) tubes.
   Vortex and incubate for 2 hours at room temperature.
9. Add 2 ml of ice cold 6% PEG*-saline solution to each tube.
   Vortex-
10. Centrifuge at a minimum of 1000 g for a minimum of 10 minutes.
11. Decant and gently blot the rim of each tube.
12. Count.

*PEG is polyethylene glycol.

B. Patient's Samples
1. Consecutively label 2 tubes for each patient's sample and control.
2. Add one ⅛" (3.2 mm) circle from the blood spots of controls and patient's samples to each appropriately labeled tube.
3. From here on steps 3-12 in Section A are followed for each patient's sample or control.

C. Calculations
1. Average the counts found in the B tubes. Subtract this blank from all tube counts except the T tube counts to obtain the corrected counts. Use only the corrected counts in the calculations.
2. Average the T tube counts to obtain the "total counts" for the assay.
3. Divide the average of the corrected MB tube counts ($B_o$) by the total counts to obtain MB, or maximum binding (0-dose).
4. Average each duplicate point and divide by $B_o$ to obtain $B/B_o$ for each point. If a duplicate determination has poor precision, say greater than 10% difference in corrected counts, calculate each tube separately.
5. Using logit-log paper prepare a calibration curve by plotting $B/B_o$ on the logit axis versus T4 concentration of the calibrator on the log axis. Draw a best-fit straight line.
6. To calculate the T4 concentration of an unknown, find the point on the concentration axis such that when a vertical line is drawn that intersects the calibration curve, the $B/B_o$ of that point on the calibration curve matches the $B/B_o$ for the unknown. The concentration value for this point is the T4 concentration of the unknown sample.

Having fully described the invention, it is intended that it be limited only by the lawful scope of the appended claims.

I claim:

1. In a process for the immunoassay of a thyronine, wherein the immunoassay consists of an incubation step in which assay tubes contain a labeled form of the thyronine, a calibrator sample or unknown samples, and an antiserum to the thyronine; followed, except in the case of homogeneous immunoassays, by a separation step in which antibody-bound thyronines are separated from free thyronines; followed by a detection step in which the amount of labeled thyronine in the bound or free fraction is determined or, in the case of homogeneous immunoassays, the change in activity such as radioactivity or enzyme activity caused by antibody-binding to some of the labeled thyronine is determined, the improvement comprising:

incubating said assay tubes each of which contain a labeled form of the thyronine, calibrator or unknown sample, and an antiserum to the thyronine at a pH above 8.9 and below the pH which causes excessive interference with the antigen-antibody reaction or with the separation of bound from free antigen, or substantial decomposition or instability of the reagents.

2. The process of claim 1 wherein the thyronine is T4.

3. The process of claim 1 wherein the thyronine is T4, and the labeled form of the thyronine is radiolabeled T4.

4. The process of claim 1 wherein the thyronine is T4, and the labeled form of the thyronine is radioiodinated T4.

5. The process of claim 1 wherein the thyronine is T4 and the labeled form of the thyronine is 125-I T4.

6. The process of claim 1 wherein the thyronine is T4 and the labeled form of the thyronine is 125-I T4, and the assay utilizes blood samples spotted on filter paper and dried.

7. The process of claim 1 wherein the thyronine is T4, the labeled form of the thyronine is 125-I T4, the assay utilizes blood samples from neonates spotted on filter paper and dried, and a double antibody separation method is utilized.

8. The process of claim 1 wherein the thyronine is T4, the labeled form of the thyronine is 125-I T4, and the separation method is double antibody.

9. The process of claim 1 wherein the separation method is double antibody.

10. The process of claim 1 wherein the labeled form of the thyronine is radiolabeled.

11. The process of claim 1 wherein the thyronine is T4, the labeled form of the thyronine is 125-I T4, the assay utilizes blood samples spotted on filter paper and dried, and the pH is at least 9.2.

12. The process of claim 1 wherein the thyronine is T4, the labeled form of the thyronine is 125-I T4, the assay utilizes blood samples from neonates spotted on filter paper and dried, and the assay is run at pH of from about 9.5 to about 10.0.

13. The process of claim 1 wherein the thyronine is 3,3′, 5-triiodothyronine (T3).

14. The process of claim 1 wherein the thyronine is T3 and the labeled form of the thyronine is radioactive T3.

15. The process of claim 1 wherein the thyronine is T3 and the labeled form of the thyronine is radioiodinated T3.

16. The process of claim 1 wherein the thyronine is T3 and the labeled form of the thyronine is 125-I T3.

17. The process of claim 1 wherein the thyronine is T3, the labeled form of the thyronine is 125-I T3, and the pH is from about 9.2 to about 10.0.

18. The process of claim 1 wherein the thyronine is T4, a radiolabeled thyronine other than T4 is used and it is labeled with iodine-125, and the assay utilizes blood samples from neonates spotted on filter paper.

19. In a process for the radioimmunoassay of thyroxine in neonates using blood samples spotted on filter paper and dried, and wherein the immunoassay consists of an incubation step in which assay tubes contain a labeled form of the thyronine, a calibrator sample or unknown sample, and an antiserum to the thyronine; followed, except in the case of homogeneous immunoassays, by a separation step in which antibody-bound thyronines are separated from free thyronines; followed by a detection step in which the amount of labeled thyronine in the bound or free fraction is determined or, in the case of homogeneous immunoassays, the change in activity such as radioactivity or enzyme activity caused by antibody-binding to some of the labeled thyronine is determined, the improvement comprising:

incubating said assay tubes each of which contain radioiodinated T4, calibrator or unknown sample, and in all except the blank tubes an antiserum to T4, at a pH of at least 8.9 and below the pH which causes excessive interference with the antigen-antibody reaction, or with the separation of bound from free antigen, or substantial decomposition or instability of the reagents.

20. In a process for the radioimmunoassay of thyroxine in neonates using blood samples spotted on filter paper and dried, and wherein the immunoassay consists of an incubation step in which assay tubes contain a labeled form of the thyronine, a calibrator sample or unknown sample, and an antiserum to the thyronine; followed, except in the case of homogeneous immunoassays, by a separation step in which antibody-bound thyronines are separated from free thyronines; followed by a detection step in which the amount of labeled thyronine in the bound or free fraction is determined or, in the case of homogeneous immunoassays, the change in activity such as radioactivity or enzyme activity caused by antibody-binding to some of the labeled thyronine is determined, the improvement comprising:

incubating said assay tubes each of which contain radioiodinated T4, calibrator or unknown sample, and an antiserum to T4 at a pH of at least 9.2, and below the pH which causes excessive interference with the antigen-antibody reaction, or with the separation of bound from free antigen, or substantial decomposition or instability of the reagents.

21. The process of claim 20 wherein the separation of bound from free antigen is carried out with a second or precipitating antibody.

22. The process of claim 20 wherein the separation of bound from free antigen is carried out with ammonium sulfate.

23. The process of claim 20 wherein the separation of bound from free antigen is carried out with polyethylene glycol.

24. The process of claim 20 wherein the separation of bound from free antigen is carried out with an adsorbant such as charcoal, coated charcoal, or talc.

25. The process of claim 20 wherein the separation of bound from free antigen is carried out with a precipitating agent such as polyethylene glycol, ammonium sulfate, or dextran.

26. The process of claim 20 wherein the separation of bound from free antigen is carried out with a solid phase antiserum.

27. The process of claim 20 wherein the separation of bound from free antigen is carried out with ethanol.

28. The process of claim 20 wherein the separation is by a solid phase antibody, either adsorbed to a solid support such as plastic, or covalently bonded to a solid support.

29. The process of claim 20 wherein the separation of bound from free antigen is carried out with solid phase antibody adsorbed to polystyrene.

30. The process of claim 20 wherein the separation of bound from free antigen is carried out with an antibody adsorbed to polyethylene.

31. The process of claim 20 wherein the separation of bound from free antigen is carried out with an antibody adsorbed to polypropylene.

32. The process of claim 20 wherein the antibody is covalently bonded to a solid support.

33. The process of claim 20 wherein the antibody is covalently bonded to a polysaccharide solid support.

34. The process of claim 20 wherein the antibody is covalently bonded to a glass solid support.

35. The process of claim 20 wherein the antibody is covalently bonded to a solid support consisting of magnetic particles.

36. The process of claim 20 wherein the separation of bound from free antigen is carried out with exclusion chromatography.

* * * * *